(12) United States Patent
Bercoff et al.

(10) Patent No.: US 10,481,260 B2
(45) Date of Patent: Nov. 19, 2019

(54) ULTRASOUND IMAGING PROBE FOR IMAGING A TEMPORARY CHANGE IN AN ENVIRONMENT

(75) Inventors: Jérémy Bercoff, Aix en Provence (FR); Claude Cohen-Bacrie, Ventabren (FR); Jacques Souquet, Puyricard (FR)

(73) Assignee: Super Sonic Imagine, Aix en Provence (FR)

( * ) Notice: Subject to any disclaimer, the term of this patent is extended or adjusted under 35 U.S.C. 154(b) by 1300 days.

(21) Appl. No.: 12/092,699

(22) PCT Filed: Aug. 3, 2007

(86) PCT No.: PCT/FR2007/051773
§ 371 (c)(1),
(2), (4) Date: May 5, 2008

(87) PCT Pub. No.: WO2008/023127
PCT Pub. Date: Feb. 28, 2008

(65) Prior Publication Data
US 2009/0149760 A1 Jun. 11, 2009

Related U.S. Application Data

(60) Provisional application No. 60/883,243, filed on Jan. 3, 2007.

(30) Foreign Application Priority Data

Aug. 22, 2006 (FR) ..................................... 06 07438

(51) Int. Cl.
*G01S 15/89* (2006.01)
*A61B 8/08* (2006.01)
(Continued)

(52) U.S. Cl.
CPC ........ *G01S 15/8918* (2013.01); *A61B 5/0053* (2013.01); *A61B 8/08* (2013.01);
(Continued)

(58) Field of Classification Search
CPC ......... A61B 8/08; A61B 8/4281; A61B 8/485; A61B 5/0053; G01S 15/8918;
(Continued)

(56) References Cited

U.S. PATENT DOCUMENTS 4,610,255 A 9/1986 Shimura et al.
5,810,731 A 9/1998 Sarvazyan
(Continued)

FOREIGN PATENT DOCUMENTS

FR 2 791 136 A1 9/2000
FR 2 844 058 A1 3/2004
(Continued)

OTHER PUBLICATIONS

Bercoff et al. Supersonic Shear Imaging: A New Technique for Soft Tissue Elasticity Mapping. IEEE Transaction on Ultrasonics, Ferroelectronics, and Frequency Control., vol. 51, No. 4, Apr. 2004; pp. 396-409.*
(Continued)

*Primary Examiner* — Thomas J Hong
*Assistant Examiner* — Helene Bor
(74) *Attorney, Agent, or Firm* — Caesar Rivise, PC

(57) ABSTRACT

The invention relates to an ultrasonic imaging probe for imaging a medium (10), comprising two types of transducers, characterized in that the first type of transducer(s) (1) is dedicated to ultrasonic imaging of the medium (10), and the second type of transducer(s) (2) is dedicated to generating a stress producing at least one transient modification of the imaged medium (10), both types of transducer(s) (1, 2) being able to operate at least in a so-called coupled mode
(Continued)

where the first type of transducer(s) (1) operates in a synchronized way with the second type of transducer(s) (2) so as to image the time course of the transient modification of the medium (10).

15 Claims, 2 Drawing Sheets

(51) Int. Cl.
   *A61B 8/00* (2006.01)
   *G01S 7/52* (2006.01)
   *A61B 5/00* (2006.01)

(52) U.S. Cl.
   CPC ............ *A61B 8/4281* (2013.01); *A61B 8/485* (2013.01); *G01S 7/52022* (2013.01); *G01S 7/52042* (2013.01); *G01S 15/8952* (2013.01); *G01S 7/52036* (2013.01)

(58) Field of Classification Search
   CPC ............ G01S 7/52022; G01S 7/52042; G01S 7/52036; G01S 15/8952
   USPC ............................. 600/443, 442; 73/579, 625
   See application file for complete search history.

(56) References Cited

U.S. PATENT DOCUMENTS

| | | | | |
|---|---|---|---|---|
| 5,984,881 | A * | 11/1999 | Ishibashi et al. | 601/2 |
| 6,068,597 | A * | 5/2000 | Lin | 600/443 |
| 6,511,427 | B1 * | 1/2003 | Sliwa et al. | 600/438 |
| 6,770,033 | B1 * | 8/2004 | Fink | A61B 8/08 |
| | | | | 600/443 |
| 6,984,209 | B2 * | 1/2006 | Hynynen et al. | 600/438 |
| 7,553,283 | B2 | 6/2009 | Sandrin et al. | |
| 2002/0070398 | A1 * | 6/2002 | Lee | 257/296 |
| 2004/0068184 | A1 * | 4/2004 | Trahey et al. | 600/437 |
| 2005/0085728 | A1 * | 4/2005 | Fukuda | 600/449 |
| 2005/0107703 | A1 * | 5/2005 | Bullis | 600/442 |
| 2005/0215899 | A1 | 9/2005 | Trahey et al. | |
| 2005/0251042 | A1 | 11/2005 | Sandrin | |
| 2005/0252295 | A1 | 11/2005 | Fink | |
| 2006/0253026 | A1 * | 11/2006 | Gueck | A61B 8/00 |
| | | | | 600/439 |

FOREIGN PATENT DOCUMENTS

| | | |
|---|---|---|
| FR | 2 844 178 A1 | 3/2004 |
| JP | 2005537835 | 12/2005 |
| WO | WO 2004/021888 | 3/2004 |
| WO | WO 2004/093686 | 11/2004 |

OTHER PUBLICATIONS

About beam geometry. (Nov. 7, 2017). Retrieved Dec. 9, 2017, from http://support.echoview.com/WebHelp/Using_Echoview/About_beam_geometry.htm.*
International Search Report for International Application No. PCT/FR07/051773.
Office Action from Chinese Application No. 201210396248.5 dated Dec. 22, 2014.
English Translation of Office Action from Chinese Application No. 201210396248.5 dated Dec. 22, 2014.

* cited by examiner

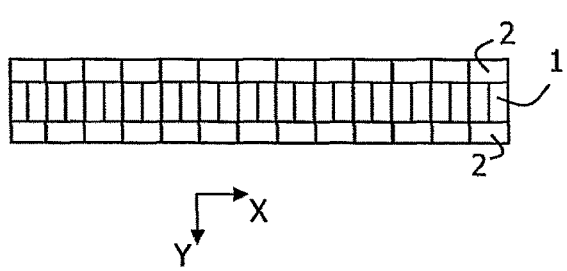
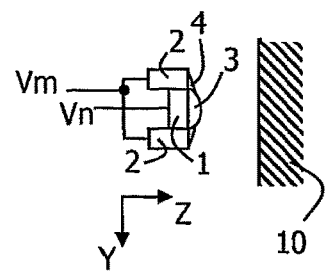
FIG.1a  FIG.1b
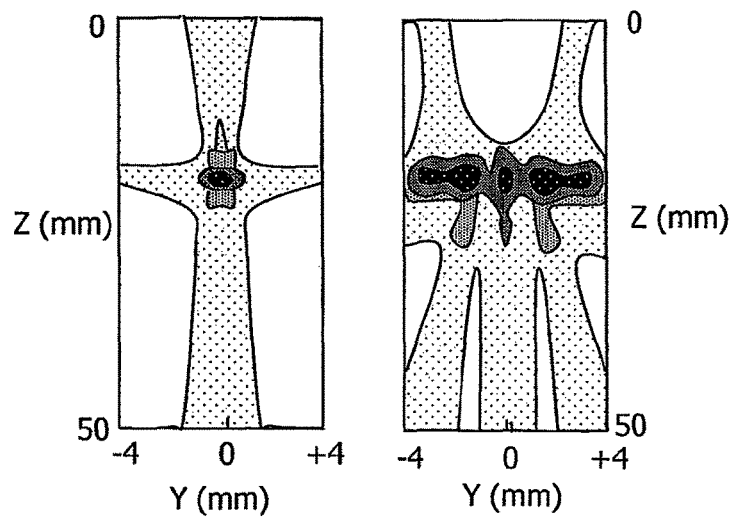
FIG.2a  FIG.2b
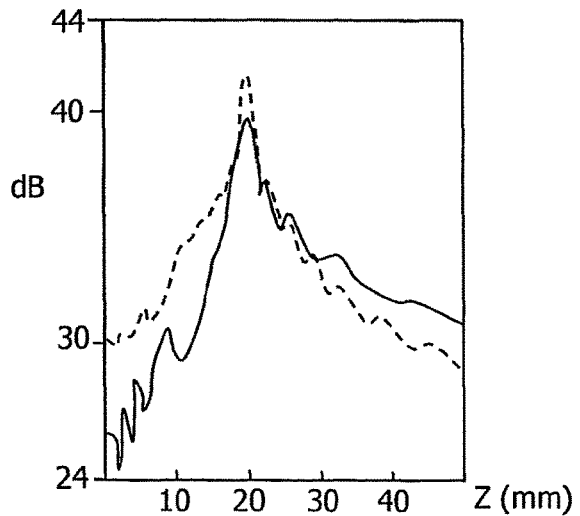
FIG.3

ULTRASOUND IMAGING PROBE FOR IMAGING A TEMPORARY CHANGE IN AN ENVIRONMENT

CROSS-REFERENCE TO RELATED APPLICATIONS

This national stage application claims the benefit under 35 U.S.C. § 371 of International Application No. PCT/FR07/051773 filed on Aug. 3, 2007, ULTRASOUND IMAGING PROBE FOR IMAGING A TEMPORARY CHANGE IN AN ENVIRONMENT, which in turn takes its priority from French Application No. 06 07438 filed on Aug. 22, 2006 and U.S. Provisional Application No. 60/883,243 filed on Jan. 3, 2007, and all of whose entire disclosures are incorporated by reference herein.

BACKGROUND OF THE INVENTION

1. Field of Invention

The present invention relates to the general field of probes intended for ultrasonic imaging, also called "echographic imaging".

The invention more particularly relates to methods and probes with which viscoelastic properties may be imaged, based on the use of ultrasonic radiation pressure.

2. Description of Related Art

Conventional echographic probes are designed for both transmitting ultrasonic waves into the tissues in a medium and sensing back-diffused signals in order to analyze them and to form an image of the medium.

Typically, these probes consist of a series of N piezoelectric transducers aligned along a line. This line may be straight or curved.

Piezoelectric transducers are individually controlled via electronic routes capable of applying electric signals out of phase with each other.

By adjusting the phases and/or delays according a cylindrical law, it is possible to focus an ultrasonic beam onto a given location in the medium, thereby electronically creating the equivalent of a lens. These laws are also used in the receiving steps in order to isolate back-diffused signals from a given location of the medium and reconstruct its acoustic image.

The size and the spacing of the transducers depend on the frequency of the ultrasonic probe and typically vary between 0.5 and 1 wavelength of the emitted ultrasonic waves.

With such a one-dimensional wave, electronic focussing and reconstruction of the ultrasonic image can only be achieved in a plane.

In the third dimension, called the "elevation", it is customary to apply on the piezoelectric transducers a fixed geometrical lens with which the ultrasonic beam may be confined on a section of reasonable thickness.

Thus, typically, the elevational size of the piezoelectric transducers is 20 wavelengths of the emitted ultrasonic wave and the geometrical focussing depth of 100 wavelengths of the emitted ultrasonic wave.

Ultrasonic waves are sometimes used for creating transient changes in the medium, for example pressure of ultrasonic radiation.

The use of ultrasonic radiation pressure is used in elastographic techniques. These techniques are imaging modes, additional to those of standard echographic imaging.

However, the use of standard echographic linear arrays particularly designed for providing a very high quality echographic image is not optimum for applying elastographic techniques and more generally for producing transient modifications within the medium.

The geometrical and acoustic properties of known probes are not suitable for generating internal mechanical stresses.

Further, the quality of the resulting elastographic images is not satisfactory.

In the case of elastographic techniques, limitations induced by known probes are three in number.

First of all, the penetration depth of the mechanical stress is limited, generally to half the potentially explorable depth.

Next, the width of the exploration area is also limited because the internal mechanical vibration source has an unsuitable geometry.

Finally, very intense acoustic fields are created so that the internal mechanical stress may be generated.

The intensity of these acoustic fields may exceed the current exposure limits and be dangerous for the patients.

OBJECT AND SUMMARY OF THE INVENTION

The main object of the present invention is therefore to find a remedy to such drawbacks by proposing a solution for generating an optimum internal mechanical stress while complying with regulatory acoustic powers and by making no compromise on the quality of the echographic imaging.

The invention therefore relates to an ultrasonic imaging probe for imaging a medium, comprising two types of transducer(s) operating at distinct frequencies, wherein the first type of transducer(s) is dedicated to ultrasonic imaging of the medium, and the second type of transducer(s) is dedicated to generating a stress producing at least a transient modification of the imaged medium, both types of transducer(s) being capable of operating at least in a so-called coupled mode where the first type of transducers operate in a synchronized way with the second type of transducers in order to image the time course of the transient modification of the medium.

With such a probe, the second type of transducer is suitable for generating a transient modification of the medium and synchronized with the first type of transducer intended to image this transient modification. Synchronization of both types of transducers is achieved depending on the physical and kinetic properties of the progression of the transient modification of the medium. The relative arrangements of the transducers may also depend on these properties.

According to an embodiment of the invention, both types of transducers are distinct by their geometrical and acoustic characteristics.

Advantageously, both types of transducers operate at distinct frequencies.

As the first transducers are dedicated to ultrasonic imaging, high quality echographic images may be obtained.

These echographic images advantageously are standard echographic images and echographic images of transient movements, in particular images of a shearing movement allowing an elastographic measurement to be made.

Thus, advantageously, the first type of transducers has two operating modes, the so-called coupled mode and a so-called standard mode where the first type of transducers produces an echographic image of the medium.

According to a particular characteristic of the invention, the stress generating a transient modification is propagative, the second type of transducer being then synchronized while taking into account the characteristics of the propagation of the stress producing the transient modification.

With such a characteristic, it is possible to directly and simply view the propagation of a wave in the medium.

Advantageously, the stress producing a transient modification is a mechanical stress by ultrasonic radiation pressure.

Such a stress allows elastography measurements to be conducted with which the elastic properties of the medium may be characterized.

In one embodiment of the invention, the transducers dedicated to ultrasonic imaging are positioned linearly. This embodiment corresponds to one of the usual formats of imaging probes and implementation of the invention in a probe similar to the existing probes allows the practitioners to get used to them quickly. The line defined by the alignment of the transducers may be straight or curved or even assume a shape adapted to the geometrical characteristics of the medium to be observed.

Advantageously, the transducers dedicated to generating the stress producing a transient modification are then distributed in two lines positioned on either side of the transducers dedicated to imaging.

The positioning of the latter transducers may again be according to a straight or curved alignment or even they may be placed according to a shape adapted to the geometrical characteristics of the medium to be observed.

According to an advantageous characteristic of the invention, the transducers dedicated to generating the stress producing a transient modification of the medium have a more remote elevational geometrical focus than the transducers dedicated to imaging.

With such a characteristic, the volume of the stress area is increased, the quality of the stress is improved and the local energy deposited in the medium is reduced.

According to another particular characteristic of the invention, the transducers dedicated to generating the stress producing a transient modification of the medium have a lower resonance frequency than that of the transducers dedicated to imaging.

In the case when radiation pressure is generated, the latter will be all the more efficient and all the deeper by means of this characteristic.

In an embodiment wherein the transducers are provided with elevational focussing lenses, these lenses are independent for both types of transducers. These focussing lenses may be implemented as a single lens having two different curvatures.

In an application of the invention, the transducers of both types are controlled via independent electronic routes and are able to be controlled synchronously.

SHORT DESCRIPTION OF THE DRAWINGS

Other features and advantages of the present invention will become apparent from the description made below, with reference to the appended drawings which illustrate an exemplary embodiment thereof without any limiting character. In the figures:

FIGS. 1a and 1b schematically illustrate a probe according to the invention,

FIGS. 2a and 2b show the aspect of the pressure fields obtained with a standard probe and a probe according to the invention, respectively, FIG. 3 illustrates the amplitude of the pressure fields versus the depth, obtained with a standard probe and with a probe according to the invention, FIG. 4 shows the attenuation of the shear field generated by the pressure fields of FIG. 3, FIGS. 5a to 5c illustrate the focussing effect for three different focuses obtained with a standard probe and a probe according to the invention.

DETAILED DESCRIPTION OF AN EMBODIMENT

FIG. 1 describes an exemplary embodiment of a probe according to the invention. The described probe is intended for an application coupling echographic imaging and elastographic imaging. More particularly, the probe may be used for breast imaging.

The described probe extends along a dimension X and has two types of transducers 1 and 2.

A first type of transducers 1, centrally positioned on the probe and illustrated as a hatched surface, is intended for imaging. The transducers 1 are for example 256 in number. They advantageously have a resonance frequency of 8 MHz and a width of 0.2 mm on the X dimension, over a height of 4 mm on the Y dimension. It is noted that for sake of clarity, in FIG. 1, the scales on X and Y are different. The transducers are controlled through 128 independent electronic routes, via a multiplexer inserted in the actual probe or placed in an echographic system to which the probe is connected. With such characteristics, the transducers 1 provide a high quality two-dimensional echographic image of the breast.

A second type of transducers 2 is intended for generating an internal mechanical stress allowing a shear wave to propagate in the medium. They are positioned linearly on either side of the transducers 1. These transducers 2 are 256 in number, i.e. 128 transducers on each side of the line formed by the transducers 1. These transducers 2 have a resonance frequency equal to half of that of the transducers of type 1, i.e. a resonance frequency equal to 4 MHz. They have a double width of 0.4 mm and half their height, i.e. 2 mm.

Both types of transducers belong to the family of ultrasonic transducers. Their resonance frequencies are above 20 kHz but they belong to distinct frequency intervals. Both types of transducers may thereby be differentiated by distinct ultrasonic resonance frequencies and by distinct geometrical properties, notably their respective sizes.

Although, in the example of FIG. 1, the number of transducers dedicated to generating the stress is the same as the number of imaging transducers, it is to be noted here that this characteristic is non-limiting, these numbers may be different.

As illustrated in the sectional view of the probe illustrated in FIG. 1b, each pair of transducers 2 located on either side of the transducers 1 are electronically coupled and controlled via the same electronic route. The 256 transducers of type 2 are therefore controlled via 128 electronic routes different from those which control the transducers of type 1.

The obtained probe is therefore controlled by an echographic system having 256 independent electronic routes.

Lenses 3 and 4 which allow elevational focussing of the thrust fields and imaging fields, respectively, are placed above the transducers 1 and 2 respectively. It is emphasized here that the lenses 3 and 4 may also be parts of a single and same lens having two different curvatures. The focussing defined by the curvature of the lens is different for the transducers 1 and the transducers 2. For the transducers 1, focussing is achieved at 20 mm whereas for the transducers 2, focussing is achieved at 60 mm.

By using different focuses, it is possible to spatially spread out the ultrasonic field intended for generating the stress while keeping an optimum confined field for echographic imaging.

Both types of transducers are controlled synchronously so as to image with the transducers 1, the progression of the transient modification of the medium caused by the transducers 2.

Advantageously, the transducers 1 have two operating modes, a first so-called standard mode where the first type of transducers produces a simple echographic image of the medium, a second so-called coupled mode where the first type of transducers operates in a synchronized way with the second type of transducers so as to image the progression of the transient modification of the medium.

Synchronization of both types of transducers is advantageously achieved according to the principles described in the French Patent Application published under number FR 2 844 058.

Insofar that the transducers 1 have the same geometrical and acoustic characteristics as those of a standard echographic linear probe, the performances of such a probe are identical from the echographic point of view, with those of a linear probe having the characteristics of the central transducers described earlier.

It is seen that these characteristics correspond to those used within the scope of mammary echography.

The performances of such a probe are analyzed in the following, for elastography.

FIG. 2a shows a pressure field in the plane (Y, Z) obtained with a one-dimensional standard probe having a focus at 20 mm.

FIG. 2b shows the pressure field in the same plane (Y, Z) obtained with a probe according to the invention as illustrated in FIG. 1.

In these figures, the intensity of the pressure field is illustrated all the more darker that this intensity is large. It is seen that in FIG. 2b, the pressure field is much more spread out over the Y direction than in the case of a standard one-dimensional probe as illustrated in FIG. 2a.

Thus, the stress generated by the probe according to the invention proves to be both more intense, as the maximum of pressure is observed over a more extended area, and better distributed. This corresponds to meeting the pursued goals, i.e. intensification of the pressure field and, consequently, generation of a shear wave particularly suitable for elastography.

FIG. 3 illustrates the amplitude of the obtained pressure fields versus depth, at the point of coordinates (0, 0, Z), with Z varying from 0 to 50 mm.

The amplitude in decibels of the pressure field obtained by the one-dimensional standard probe is illustrated in dotted lines, and the amplitude of the pressure field for the probe according to the invention is illustrated in solid lines.

It is noted that at the focussing point at 20 mm, the pressure field for the probe according to the invention is 3 decibels lower than that for the standard one-dimensional probe.

Nevertheless, this parameter is less important for applying an elastographic method than the propagation length of the shear wave created by the pressure field.

The aforementioned pressure fields indeed create a source of shear.

Figure 4:
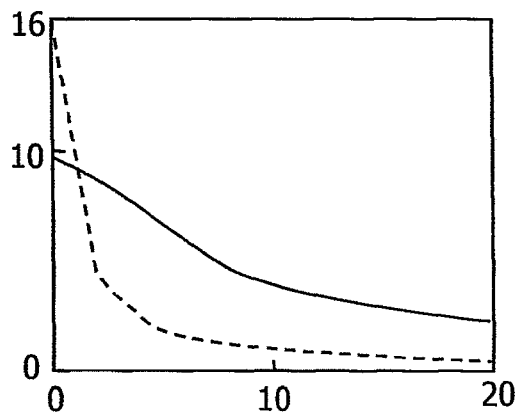

In FIG. 4, the damping of the shear field created by the aforementioned pressure fields is illustrated as a displacement D depending on the lateral distance X to the source.

With this, it is possible to compare the resulting shear waves for two probes with focussing at 20 mm.

It is noted that if the displacement field is less significant at the centre of the source with the probe according to the invention (solid line), it is much less faster damped than for the standard probe (dotted line) and is even four times more intense after having propagated over two centimeters.

This is due to the spreading out of the shear source in the elevational direction Y as illustrated in FIG. 2b. This allows the shear field to be less diffracting outside the plane of the imaging.

Thus, with the invention, it is possible to generate a shear wave of better quality while locally inducing a less intense pressure field. In the cases when the regulatory limits of acoustic powers are a constraint, this may prove to be very advantageous.

Additionally, interest in the penetration depth of the shear source is required in order to apply an elastographic method in a satisfactory way. Indeed, in order to use an elastographic method in a satisfactory way, it is necessary to focus and to create a shear wave as deep as the depth which is otherwise imaged by echography.

This imposes that the transducers 2 be transducers operating at a lower frequency than the transducers 1 intended for echography. Otherwise, as this is the case with a standard probe, the focussing effect is limited to about half the imaging depth and this because of ultrasonic damping.

Figures 5A, 5B, 5C:
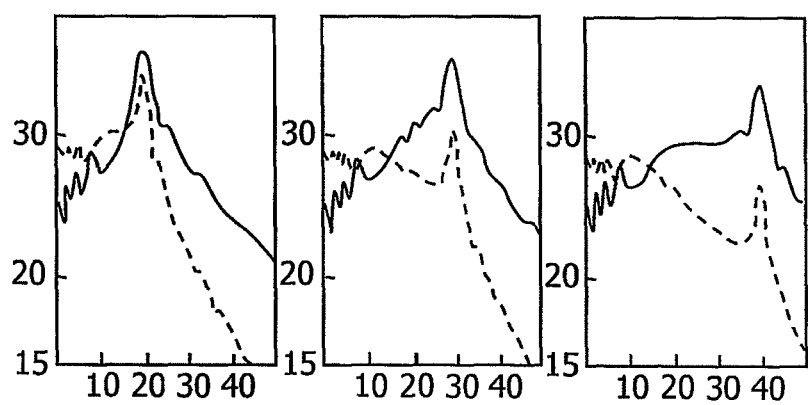

FIGS. 5a to 5c illustrate this for focuses at 20, 30 and 40 mm from each of the standard probes and those according to the invention, respectively. These figures illustrate the fields of pressures created by both probes over a Z depth of 50 mm.

It is seen that the probe according to the invention (solid line) allows a shift into the medium at more than 40 mm, whereas the penetration depth of the standard probe is of the order of about twenty millimeters.

It is finally noted that different applications may be performed by one skilled in the art according to the principles of the invention as defined in the following claims. Notably, the arrangement of the transducers may be varied. The transducers 1 and 2 may thus be superimposed over each other. In this case, only the imaging transducers 1 remain visible for the operator, the transducers 2 being placed "behind" the transducers 1 and consequently hidden by the latter. The number and the shape of the transducers of each type may also be diverse. It is possible to use more transducers 1 and less transducers 2 and vice versa.

It is also seen that the transducers of the second type, or part of them, although specifically adapted to generating stress, may also be used for producing echographic imaging in a coupled mode, for example before and after generating the stress, and this so as to cover a wider imaging area in the elevational direction than with only transducers of the first type. With the exemplary probe proposed in FIG. 1, simultaneous imaging then becomes possible in a coupled mode in three distinct imaging planes.

It is also seen that the transducers of the first type, or part of them, may also be used for generating a stress in addition to the one specifically generated by the transducers of the second type.

What is claimed is:
1. An ultrasonic imaging probe for imaging a medium, comprising:
   a first type of ultrasonic transducers configured to perform an ultrasonic imaging of the medium, having a first focus in the medium and a first resonance frequency, and a second type of ultrasonic transducers configured to generate a stress producing transient movements of the imaged medium, having a second focus in the medium and a second resonance frequency, wherein the second focus generates said stress producing transient movements as deep as depth of ultrasonic imaging obtained with the first focus, and the second resonance frequency is lower than the first resonance frequency, the first and the second types of ultrasonic transducers having different focuses so that field of said stress producing transient movements is larger than field of said ultrasonic imaging while maintaining said probe in a fixed position relative to said medium, the first and the second types being configured to operate at least in a coupled mode wherein the first and the second types are synchronized so as to image the medium during progression of the transient movements to obtain images of progression of transient modification of the medium.

2. The probe according to claim 1, wherein the first and the second types of transducers have distinct geometrical and acoustic characteristics.

3. The probe according to claim 1, wherein the stress is propagative, the second type of transducers being synchronized while taking into account characteristics of a propagation of the stress.

4. The probe according to claim 3, wherein the stress producing transient movements is a mechanical stress by ultrasonic radiation pressure.

5. The probe according to claim 1, wherein the transducers of the first type are positioned linearly.

6. The probe according to claim 1, wherein the transducers of the second type are distributed in two lines positioned on either side of the transducers of the first type.

7. The probe according to claim 1, wherein both the first and the second types of transducers are provided with independent elevational focusing lenses.

8. The probe according to claim 1, wherein both types of transducers are controlled via independent electronic routes and arranged to be controlled synchronously.

9. The probe according to claim 1, wherein the transient movements include shearing movements.

10. The probe according to claim 1, wherein the transient modification includes transient movements.

11. An ultrasonic imaging probe according to claim 1, wherein at least the first type or the second type of ultrasonic transducers has a lens in front thereof.

12. An ultrasonic probe according to claim 1, wherein the second type of ultrasonic transducers are configured to generate the stress producing transient movements at more than 40 mm into the imaged medium.

13. An ultrasonic imaging probe for imaging a medium, comprising:

a first type of ultrasonic transducers configured to perform an ultrasonic imaging of the medium, having a first focus in the medium and a first resonance frequency, and a second type of ultrasonic transducers configured to generate a stress producing a transient movements of the imaged medium, having a second focus in the medium and a second resonance frequency, wherein the second focus generates said stress producing transient movements as deep as depth of ultrasonic imaging obtained with the first focus, and the second resonance frequency is lower than first resonance frequency, the first and second types of ultrasonic transducer having different focuses so that field of said stress producing transient movements is larger than field of said ultrasonic imaging while maintaining said probe in a fixed position relative to said medium, the first and the second types being configured to operate at least in a coupled mode wherein the first and the second types are synchronized so as to image the medium during progression of the transient movements to obtain images of progression of transient modification of the medium, and the second type of ultrasonic transducers have a focus in the medium deeper than a further focus of the first type of ultrasonic transducers.

14. An ultrasonic probe according to claim 13, wherein at least the first type or the second type of ultrasonic transducers has a lens in front thereof.

15. An ultrasonic probe according to claim 13, wherein the second type of ultrasonic transducers are configured to generate the stress producing transient movements at more than 40 mm into the imaged medium.

* * * * *